United States Patent
Koogle, Jr. et al.

(10) Patent No.: US 8,911,457 B2
(45) Date of Patent: Dec. 16, 2014

(54) METHOD OF USING KNOT PUSHER AND SUTURE CUTTER INSTRUMENT

(75) Inventors: David C. Koogle, Jr., Naples, FL (US); Jerry F. Sterrett, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1071 days.

(21) Appl. No.: 12/397,213

(22) Filed: Mar. 3, 2009

(65) Prior Publication Data

US 2009/0228026 A1    Sep. 10, 2009

Related U.S. Application Data

(60) Provisional application No. 61/033,653, filed on Mar. 4, 2008.

(51) Int. Cl.
A61B 17/04    (2006.01)
(52) U.S. Cl.
CPC ......... *A61B 17/0469* (2013.01); *A61B 17/0467* (2013.01); *A61B 2017/0474* (2013.01)
USPC .......................................................... 606/148
(58) Field of Classification Search
CPC .............................................. A61B 2017/0474
USPC ........................................ 606/139, 144–150
See application file for complete search history.

(56) References Cited

U.S. PATENT DOCUMENTS

| | | | | |
|---|---|---|---|---|
| 7,717,927 | B2 * | 5/2010 | Hahn et al. | 606/148 |
| 8,109,945 | B2 * | 2/2012 | Boehlke | 606/148 |
| 8,211,123 | B2 * | 7/2012 | Gross et al. | 606/148 |
| 8,252,005 | B2 * | 8/2012 | Findlay et al. | 606/139 |
| 8,603,125 | B2 * | 12/2013 | Stone et al. | 606/170 |
| 2003/0040760 | A1 * | 2/2003 | Hnojewyj et al. | 606/148 |
| 2004/0162569 | A1 * | 8/2004 | Sikora et al. | 606/148 |
| 2007/0173865 | A1 | 7/2007 | Oren et al. | |

* cited by examiner

*Primary Examiner* — Melanie Tyson
(74) *Attorney, Agent, or Firm* — Dickstein Shapiro LLP

(57) ABSTRACT

A combined knot pusher/suture cutter device for manipulating a knotted suture to properly locate the knot relative to the tissue being sutured, and then for removing excess suture from the knot. The knot pusher/suture cutter includes a body member with a handle and an inner member (or inner rod) having a knot-engageable section at the opposite end (distal end) for engaging and moving the knotted suture by manipulation of the handle. The knot-engageable section of the inner member is provided with a slot at its distal end which allows suture to be threaded through it. The inner member is provided within an outer sleeve that is designed to be actuated by a spring and a thumb pusher (trigger) located on a surface of the handle. By actuating the thumb trigger (for example, by sliding forward the thumb trigger), the outer sleeve is advanced and the suture post is cut.

4 Claims, 6 Drawing Sheets

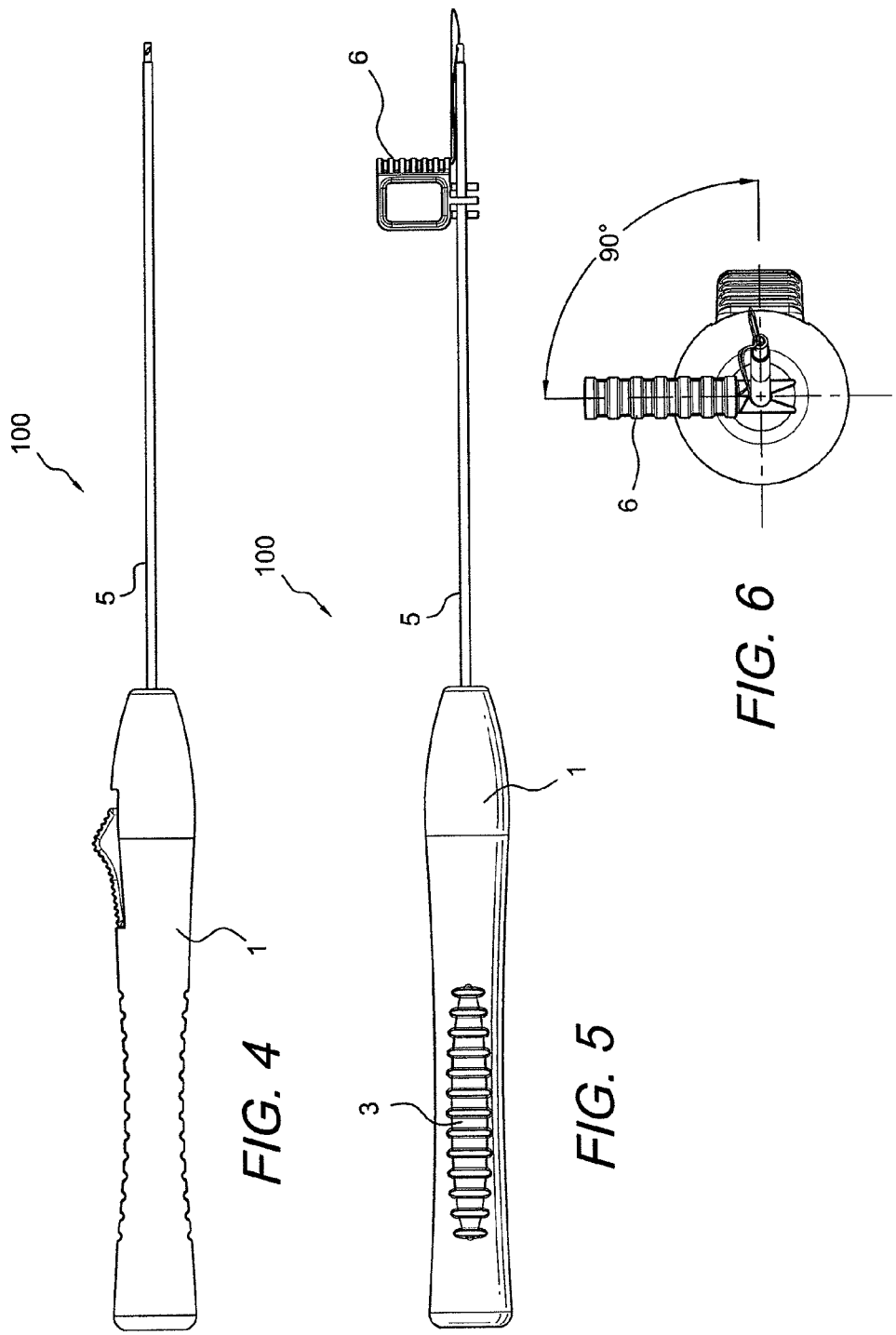

METHOD OF USING KNOT PUSHER AND SUTURE CUTTER INSTRUMENT

CROSS-REFERENCE TO RELATED APPLICATIONS

This application claims the benefit of U.S. Provisional Application No. 61/033,653, filed Mar. 4, 2008, the entire disclosure of which is incorporated by reference herein.

FIELD OF THE INVENTION

The present invention relates to methods of arthroscopic surgery and, more specifically, to an improved knot pusher/suture cutter instrument used for manipulating suture during methods of tissue repair.

BACKGROUND OF THE INVENTION

Tissue repair typically requires the surgeon to pass suture material through selected tissue, form a plurality of surgical knots extracorporeally and then move the knots into position adjacent the desired tissue to be sutured. In such procedures, the surgeon must tie the knots on the suture strands after the suture is threaded through the selected tissues to be sutured, and then cut the remaining suture strands from the surgical site. High strength suture materials, such as FiberWire®, for example, are difficult to cut mainly because of their increased strength.

An improved surgical instrument that acts both as a knot pusher instrument (forcing the knots down into the proper position) and as a suture cutter (cutting the ends of suture) is needed. An instrument that cuts suture clean and without difficulty, regardless of the strength of the suture material, is also needed.

SUMMARY OF THE INVENTION

The present invention provides a combination knot pusher/suture cutter device for manipulating a knotted suture to properly locate the knot relative to the tissue being sutured, and then for removing excess suture from the knot.

The combination knot pusher/suture cutter device of the present invention comprises a body member including a handle and an inner member (or inner rod) having a knot-engageable section at the opposite end (distal end) for engaging and moving the knotted suture by manipulation of the handle. The knot-engageable section of the inner member comprises a slot at its distal end which allows suture to be threaded through it. The inner member is provided within an outer sleeve that is designed to be actuated by a spring and a thumb pusher (trigger) located on a surface of the handle. By actuating the thumb trigger (for example, by sliding forward the thumb trigger), the outer sleeve is advanced and the suture post is cut.

Other features and advantages of the present invention will become apparent from the following description of the invention, which refers to the accompanying drawings.

BRIEF DESCRIPTION OF THE DRAWING

FIG. 4 illustrates a side view of the combined knot pusher/suture cutter assembly of FIG. 1;

FIG. 5 illustrates another side view (rotated 90 degrees) of the combined knot pusher/suture cutter assembly of FIG. 1 (with suture threader attached);

FIG. 6 illustrates a top view of the combined knot pusher/suture cutter assembly of FIG. 5;

DETAILED DESCRIPTION OF THE PREFERRED EMBODIMENTS

Figure 1:
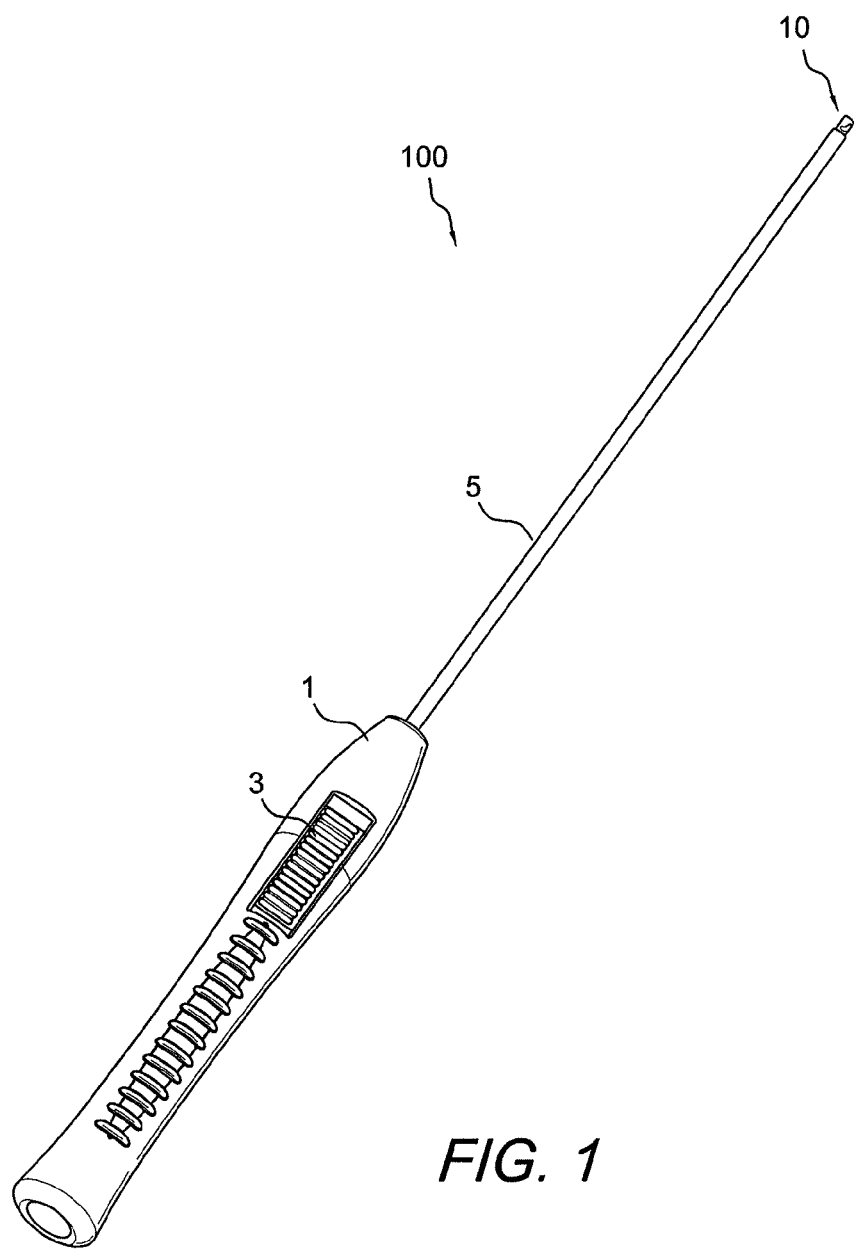
FIG. 1 illustrates a perspective view of a combined knot pusher/suture cutter assembly according to an embodiment of the present invention.
Figure 2:
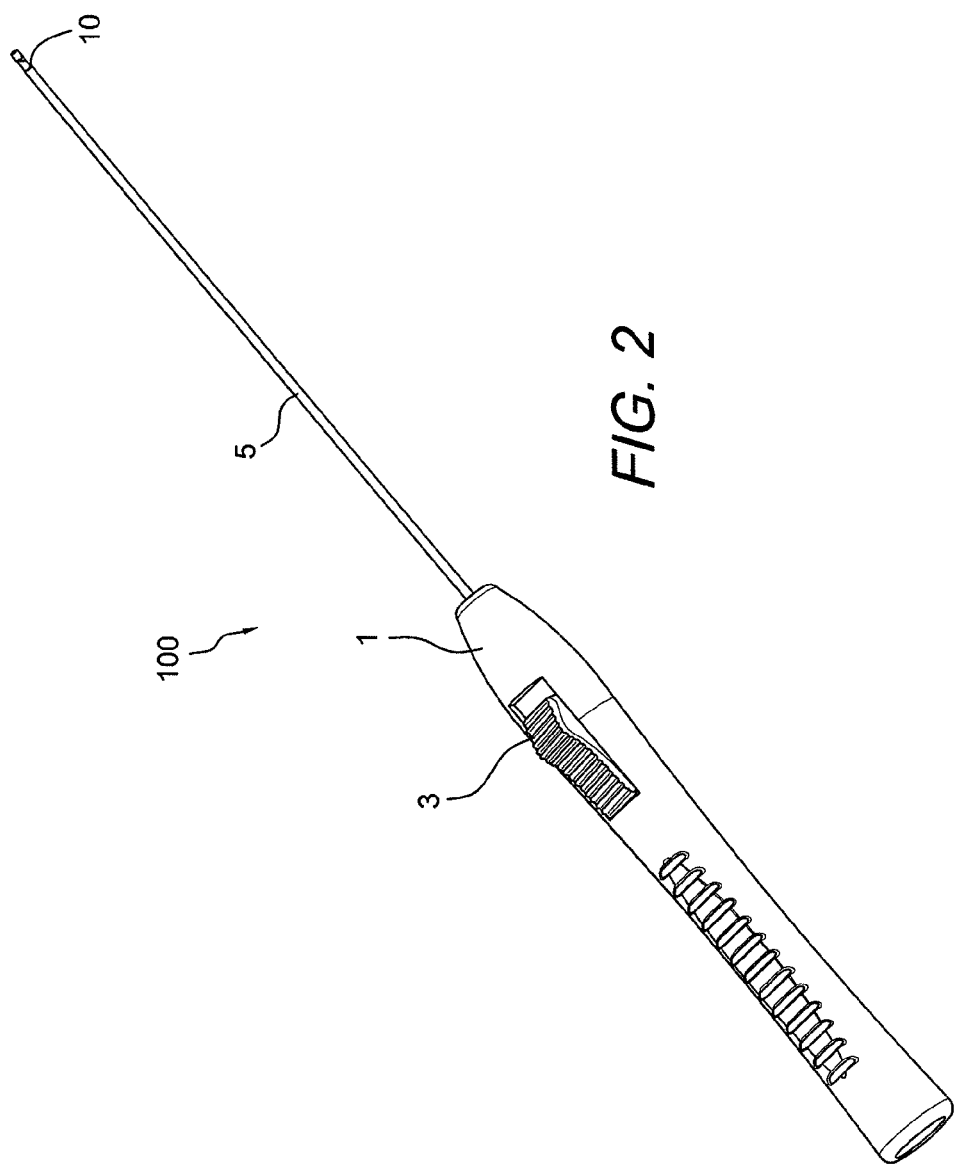
FIG. 2 illustrates another perspective view of the combined knot pusher/suture cutter assembly of FIG. 1.
Figure 3:
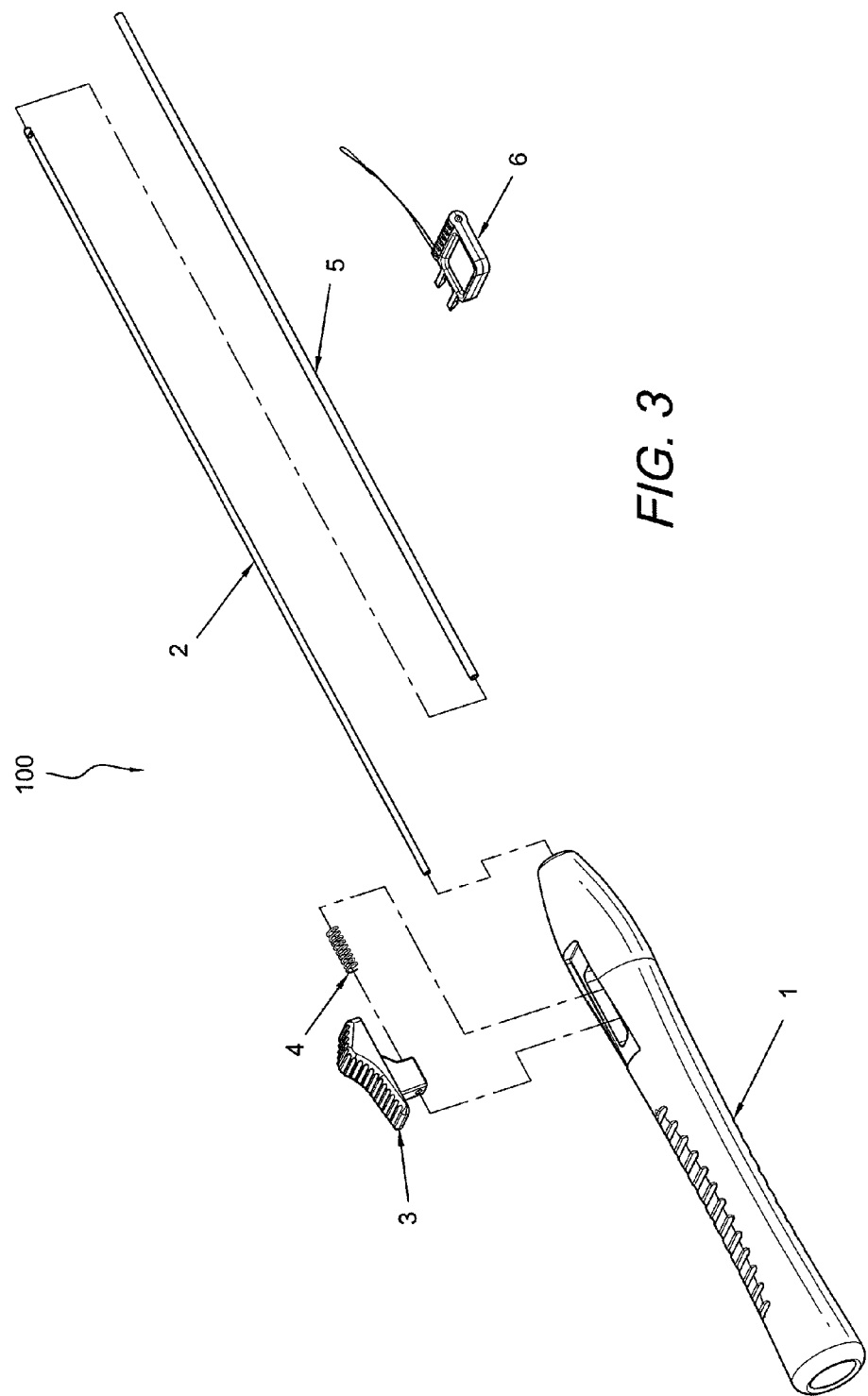
FIG. 3 illustrates an expanded view of the distal end of the combined knot pusher/suture cutter assembly of FIG. 1.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a combination knot pusher/suture cutter device for manipulating a knotted suture to properly locate the knot relative to the tissue being sutured, and then for removing excess suture from the knot. The combined knot pusher/suture cutter assembly of the present invention comprises a body member including a handle and an inner member (or inner rod) having a knot-engageable section at the opposite end (distal end) for engaging and moving the knotted suture by manipulation of the handle. The knot-engageable section of the inner member comprises a slot at its distal end which allows suture to be threaded through it. The inner member is provided within an outer sleeve that is designed to be actuated by a spring and a thumb pusher (trigger) located on a surface of the handle. By actuating the thumb trigger (for example, by sliding forward the thumb trigger), the outer sleeve is advanced and the suture post is cut.

Referring now to the drawings, where like elements are designated by like reference numerals, FIGS. 1-8 illustrate a combined knot pusher/suture cutter assembly 100 of the present invention. As shown in the drawings, the combined knot pusher/suture cutter assembly 100 comprises a handle 1, an inner rod or inner tube 2 disposed within an outer tube 5, a thumb pusher (trigger) 3 in communication with a spring 4, and a suture threader 6 that is configured to securely engage the outer tube 5. A knot-engageable/suture cutter section 10 is provided at most distal end of the knot pusher/suture cutter assembly 100 as shown, for example, in FIG. 7.

Figure 7:
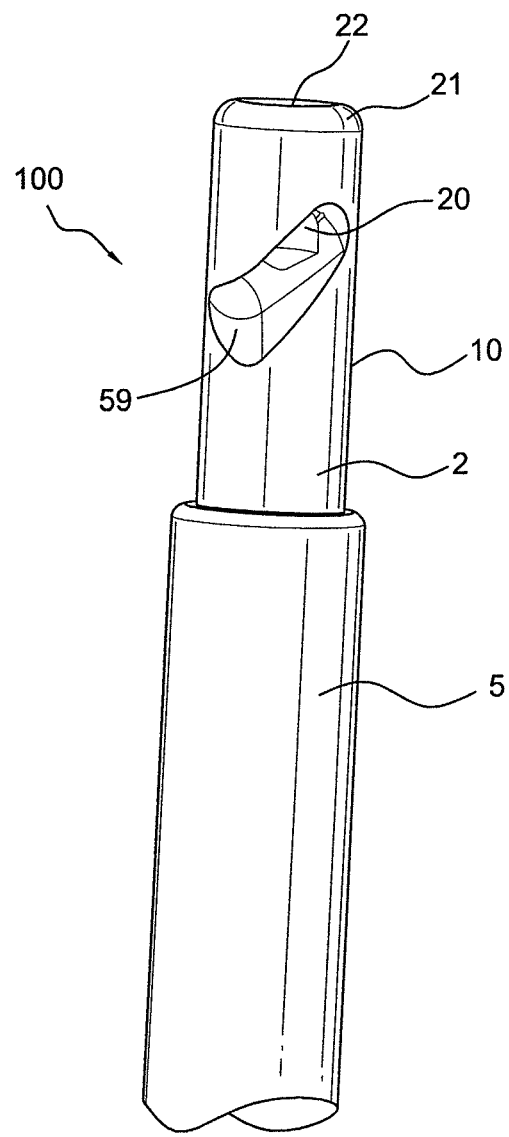
FIG. 7 illustrates an expanded view of the distal end of the combined knot pusher/suture cutter assembly of FIG. 1.
Figure 8:
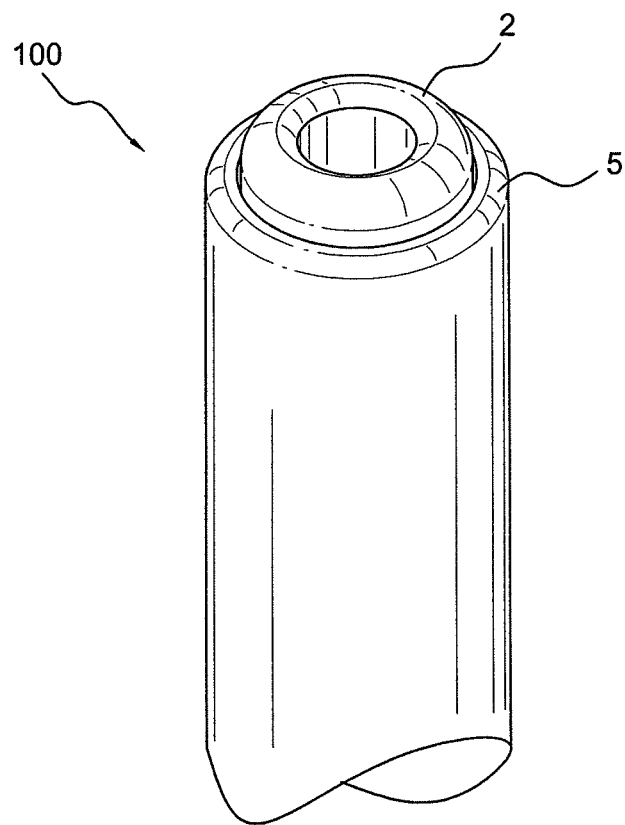
FIG. 8 illustrates an expanded view of the distal end of the combined knot pusher/suture cutter assembly of FIG. 7 (in the advanced or post-cut position).

As more clearly illustrated in FIG. 7, inner rod 2 is provided at its most distal end with knot-engageable/suture cutter section 10 that includes a slot 20 which is designed to allow suture to be threaded through it. Slot 20 is in communication with opening 22 (FIG. 7) located at a most distal end 21 of inner rod 2. Knot-engageable/suture cutter section 10 also a cutting edge 59 (FIG. 7) for cutting suture passing through the slot 20.

Referring now to FIGS. 3-6, a method of assembling the combined knot pusher/suture cutter assembly 100 begins by orienting the slot of suture threader 6 (FIG. 3) with the slot of the handle (both slots facing up and forming an angle of about 90 degrees), as shown in FIG. 6. The inner rod 2 is sled into the handle 1 with thumb pusher 3 and spring 4 aligned in handle slot. Once alignment is achieved, the inner rod 2 is pressed into handle 1 until bottomed out. Although suture threader 6 may be positioned at about 90 degrees, this position is not necessary. Outer tube 5 is then slid onto inner rod 2 and pressed into the thumb pusher. When the outer tube 5 is advanced over inner rod 2, the thumb pusher should move easily.

A flexible strand such as a suture strand (for example, a high strength suture such as FiberWire®) is threaded from the suture threader 6 into the slot 20 of the inner rod 2 so that the suture exits the hole with about 0.5 in stickout. The suture threader 6 may then be securely attached to the shaft of the outer tube 5, by snapping the threader to the tube, for example.

In use, the surgeon first threads the suture post through the opening 22 at the distal tip using the suture threader attached to the outer tube, so that it exits out through the slot 20 before the outer sleeve 5. The surgeon then will hold tension on the post, with one hand, and advance the device 100 forward (with the other hand) to slide the knot down until the suture construct is tightly secured. Then the surgeon will slide the thumb trigger 3 forward to advance the outer sleeve 5 and cut the suture. Spring 4 within the handle 1 is designed to return the thumb trigger 3 back to the original position, which (in turn) allows the outer sleeve 5 to move back as well.

The combined knot pusher/suture cutter assembly 100 of the present invention is designed to act both as a knot pusher instrument (forcing the knots down into the proper position) and as a suture cutter (cutting the ends of suture). The instrument 100 of the present invention is also designed to cut suture clean and without difficulty, regardless of the strength of the suture material. A special application of the instrument 100 of the present invention is for cutting FiberWire® cleanly and without difficulty. Because of its strength, FiberWire® cannot be cleanly cut by scissoring or clipping (pinching). By sliding the Fiberwire® along a sharp edge, in a relatively short distance, it can be cut cleanly. With the knot pusher/suture cutter assembly 100 of the present invention, because the slot 20 on the inner shaft 2 is at an angle to the outer sleeve 5 and the longitudinal axis of the shaft, the FiberWire® is forced to slide along a sharp edge, thus being cut cleanly.

The combined knot pusher/suture cutter assembly 100 of the present invention has also particular application to advancing knots and cutting suture during methods of tissue repair employing cinch stitching. In this particular application, the instrument 100 of the present invention may be employed to push knots and/or cut suture posts once the suture implant constructs have been deployed within the meniscal tissue to be repaired (by using a plurality of first and second trocars carrying the implants on their external surfaces, for example).

The present invention also provides methods for meniscal repair by cinch stitching. According to an exemplary embodiment, the method comprises the steps of: (i) providing a meniscal cinch assembly comprising first and second trocars, a depth stop adapted to securely engage one of the trocars, and a suture implant construct having first and second implants loaded on the external surface of the first and second trocars; (ii) passing at least one of the first and second implants through tissue to be repaired (for example, the meniscal tissue); and (iii) pushing knots and/or cutting suture material attached to the first and second implants with the combined knot pusher/suture cutter assembly 100 of the present invention.

The combined knot pusher/suture cutter assembly 100 described above may be also employed in additional surgical applications that require knot formation and suture cutting, for example, in shoulder applications where the device may be employed as both a knot pusher and a suture cutter.

For the purposes of the present invention, the term "high strength suture" is defined as any elongated flexible member, the choice of material and size being dependent upon the particular application. For the purposes of illustration and without limitation, the term "suture" as used herein may be a cable, filament, thread, wire, or any other flexible member suitable for tissue fixation in the body. In a preferred embodiment of the invention, and as described above, the suture comprises a high strength suture sold by Arthrex, Inc. under the tradename FiberWire®.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of advancing suture to tighten a knot and of cutting the suture, the suture extending from a surgical site at which the knot is to be positioned, the method comprising the steps of:

providing a knot pusher/suture cutter instrument comprising an inner member disposed coaxially within an outer tube; a cutting section located at a distal end of the inner member, the cutting section being provided with an opening for passing suture therethrough and with a sharp cutting edge for cutting the suture, the opening being in communication with an axial opening located at a most distal end of the inner member, the opening on the inner member forming an angle relative to the outer tube and to a longitudinal axis of the knot pusher/suture cutter instrument to allow cutting of the suture, by forcing the suture to slide along the sharp cutting edge of the opening; and an actuator assembly coupled with the outer tube;

positioning the instrument proximal to the knot to be advanced;

threading the suture through the opening at the distal end so that the suture exits out of the axial opening;

holding tension on the suture with one hand and advancing the instrument with the other hand to engage the knot with a distal end of the inner member and to move the knot toward the surgical site; and actuating the actuator assembly to advance the outer tube toward the inner member and to force the suture to slide along the sharp cutting edge of the opening of the inner member, and to cut the suture with the sharp cutting edge of the opening.

2. The method of claim 1, wherein the step of actuating the actuator assembly comprises pushing forward a trigger to move the outer tube relative to the inner member a predetermined distance.

3. The method of claim 1, wherein the suture is a high strength suture comprising ultrahigh molecular weight polyethylene.

4. The method of claim 1, further comprising providing a suture threader attached to the outer tube, and then threading a suture post of the suture through the axial opening at the most distal end of the inner member using the suture threader.

* * * * *